United States Patent [19]

Wick

[11] Patent Number: 5,123,900
[45] Date of Patent: Jun. 23, 1992

[54] MOISTURE PERMEABLE DOUBLE DISK

[75] Inventor: John J. Wick, Williston, Vt.

[73] Assignee: Bertek, Inc., Swanton, Vt.

[21] Appl. No.: 746,764

[22] Filed: Aug. 16, 1991

[51] Int. Cl.⁵ .............. A61F 15/00; A61F 13/00; A61L 15/00

[52] U.S. Cl. ..................... 602/41; 602/42; 602/43; 602/47; 602/48; 602/54; 602/55; 602/57; 602/59

[58] Field of Search ............... 128/156, 155; 602/41–59

[56] References Cited

U.S. PATENT DOCUMENTS

| | | | |
|---|---|---|---|
| 2,877,765 | 3/1959 | Bunjan | 128/156 |
| 4,499,896 | 2/1985 | Heinecke | 128/155 |
| 4,573,996 | 3/1986 | Kwiatek et al. | |
| 4,787,888 | 11/1988 | Fox | |
| 4,841,962 | 6/1989 | Berg et al. | 128/156 |
| 4,915,102 | 4/1990 | Kwiatek et al. | |
| 5,018,515 | 5/1991 | Gilman | 128/156 |

FOREIGN PATENT DOCUMENTS

8907959  9/1989  World Int. Prop. O. .......... 128/156

Primary Examiner—Randall L. Green
Assistant Examiner—Dinh X. Nguyen
Attorney, Agent, or Firm—Lerner, David, Littenberg, Krumholz & Mentlik

[57] ABSTRACT

Skin contact devices are disclosed for treating the skin, including a film layer which is non-occlusive to the passage of water vapor, an occlusive layer adhesively affixed to the inner surface of the film layer, in which the occlusive layer does not permit water vapor to pass therethrough, and a series of vent slots extending through the occlusive layer so that water vapor contained within the occlusive layer can pass through these vents for subsequent passage through the film layer itself.

27 Claims, 3 Drawing Sheets

MOISTURE PERMEABLE DOUBLE DISK

FIELD OF THE INVENTION

The present invention relates to skin contact devices. More particularly, the present invention relates to devices for administering medicaments such as active agents to the skin and holding same in place thereon.

Still more particularly, the present invention relates to wound dressings which include various medicaments thereon for placement against the skin. Still more particularly, the present invention relates to transdermal devices for the application of various drugs through the skin to a patient.

BACKGROUND OF THE INVENTION

The field of skin contact devices in general and transdermal devices in particular has undergone significant development in the last several years. With respect to the application of film layers broadly, that is with or without an active agent medicament therewith, there has been a general development based upon the discovery in the early 1970's, contrary to previous beliefs, that the healing of wounds occurs significantly faster and with less scar formation when it takes place under a film which is capable of maintaining a well-balanced moist environment, such as that which naturally occurs under a blister.

In view of this understanding, a number of different medical and surgical dressings were developed, leading most recently to the devices which are shown and disclosed in U.S. Pat. No. 4,915,102. In the background section of that patent, there is a detailed discussion of a number of other devices which had been developed prior to that time, and whose function was to provide various types of wound dressings taking advantage of this discovery.

With respect to the specific field of transdermal application, in addition to the fact that the above-mentioned U.S. Pat. No. 4,915,102 also specifically discloses devices for applying both a film layer and an active agent carrier, a number of other such devices have also been developed.

Thus, predecessors to the devices shown in U.S. Pat. No. 4,915,102 include devices such as those shown in U.S. Pat. No. 4,573,996. These devices each include a reservoir of an active agent, a release mechanism for releasing the active agent through the skin of the patient, and an outer layer which is variously described as being "occlusive." Thus, in the particular environment in question, these layers are required to be impermeable to the active agent itself, so as to prevent its escape, and are also impermeable to the passage of water vapor therethrough.

Another wound dressing is shown in U.S. Pat. No. 4,499,896. In this patent a wound dressing is disclosed, which includes a first layer 2, which is to be placed over the wound and which is impermeable to liquid water, but which has a moisture-vapor permeability of at 300 g/m$^2$ for 24 hours at 80% relative humidity differential at 40° C., and which includes perforations 3 for passing wound exudate through the first layer, and which also includes an imperforate second layer 5 which is impermeable to liquid water and has a moisture-vapor permeability of at least 600 g/m$^2$ for 24 hours at 80% relative humidity differential at 40° C. A reservoir is thus formed between the two layers to which wound exudate passes by way of the perforations of the first layer, and which then slowly evaporates to the second layer. The reservoir itself can also include a medicament.

Also, U.S. Pat. No. 4,787,888 discloses a drug delivery device which, in this case, employs a piezoelectric polymer element coupled with a sonic generator for supplying energy to produce sonic vibrations to drive the medicament into the skin. In this device the drug matrix layer 32 is located between the piezoelectric polymeric body and the skin, and the former includes polymer films 16 and 18, which are superimposed by a flexible film cover element 20. FIGS. 1 and 3 of this patent appear to illustrate the central layers 54 and 55 in bimorphs as having wide, perpendicular slits having an opening between the drug layer and the flexible cover layer. There is no discussion, however, in the specification regarding the presence of any such slits, let alone their purpose.

Column 3, lines 53–58 of this patent, in fact, refer to the assembly from "plural components." In any event, the piezoelectric material disclosed in this patent is PVDF, which is moisture-impermeable and, since the overall piezoelectric polymer layer includes layer 20, even the slits shown therein do not extend to the outer surface, i.e., they are covered by another water vapor-impermeable layer.

Problems have thus continued with a number of these transdermal devices and the like in maintaining skin contact and flawlessly performing the function thereof, particularly for extended periods of time. Thus, the principal objects of delivering the drug at a constant rate by maintaining complete contact with the skin over long periods of time have continued to require improvements. One factor which exacerbates this problem is the build-up of moisture within these devices. Another such factor is the relative stiffness of certain of these devices, which facilitates their eventual unintended removal from the surface of the skin.

SUMMARY OF THE INVENTION

In accordance with the present invention, these and other objects have now been realized by applicant's discovery of a skin contact device for treating the skin of a patient, such as by applying a medicament to the skin of a patient, which comprises a film layer, which is thin and flexible and which is non-occlusive to the passage of water vapor, the film layer including an outer surface, an inner surface, and an outer periphery, an adhesive layer on the inner surface of the film layer for maintaining the film layer on the skin, an occlusive layer disposed on the inner surface of the film layer, the occlusive layer including an outer surface in adhesive contact with the film layer and an inner surface, the occlusive layer being occlusive to the passage of water vapor and having an outer periphery contained fully within the outer periphery of the film layer, and vent means between the inner surface of the occlusive layer and the film layer permitting the free passage of water vapor contained within the occlusive layer through the vent means for passage through the film layer. In a preferred embodiment the occlusive layer includes a medicament on its inner surface.

By employing the skin contact device of this invention, it is therefore now possible to extend the period of use during which these devices remain on the skin. Thus, as compared to many of the present such devices which will remain on the skin for one day, or possibly up to a maximum of about three days, with the present devices this can be extended, such as for periods of up to one week or possibly even longer. This, of course, translates into significant consumer advantages and considerable convenience and safety as compared to the prior art. Furthermore, the devices of this invention can also provide for highly improved articulation, so that these skin contact devices, even if placed at skin locations, such as the hand, which are subject to constant movement and use, will nevertheless remain in firm contact with the skin. The clear advantages of same should be quite apparent.

In accordance with one embodiment of the skin contact device of the present invention the occlusive layer is substantially continuous except for the vent means. In another embodiment, however, the occlusive layer comprises a plurality of separate occlusive portions separated by the vent means.

In accordance with a preferred embodiment of the skin contact device of the present invention, the vent means comprises slit means extending through preselected portions of the occlusive layer. Preferably, the slit means comprise a plurality of slits extending through the occlusive layer.

In a highly preferred embodiment, the plurality of slits includes a first plurality of slits extending radially from a central location on the occlusive layer.

In accordance with another embodiment of the skin contact device of the present invention, medicament comprises a systemic or topical drug composition, and preferably includes a drug enhancer.

In accordance with another embodiment of the skin contact device of the present invention, the occlusive layer comprises a first occlusive layer, and the device includes a second occlusive layer, and the vent means comprises first vent means, the second occlusive layer including an outer surface in contact with the inner surface of the first occlusive layer, and an inner surface, the second occlusive layer being occlusive to the passage of water vapor and having an outer periphery contained fully within the outer periphery of the film layer, and second vent means between the inner surface of the second occlusive layer and the first occlusive layer permitting the free passage of water vapor contained within the second occlusive layer through the second vent means for passage through the first vent means and through the film layer. Preferably, the inner surface of the second occlusive layer includes a medicament.

In a preferred embodiment, the first vent means is maintained at a location which is displaced from the location of the second vent means, whereby the water vapor cannot pass directly through the first vent means to the second vent means.

In accordance with this embodiment of the skin contact device of the present invention, the first and second occlusive layers are substantially continuous except for the first and second vent means. Preferably, the first and second vent means comprise slit means extending through preselected portions of the first and second occlusive layers, and in a highly preferred embodiment the slit means comprises a plurality of slits extending through the first and second occlusive layers.

In accordance with another embodiment of the skin contact device of the present invention, the device includes a release layer disposed on the inner surface of the occlusive layer, the surface of the release layer in contact with the medicament comprising a releasable surface. Preferably, the releasable surface is a siliconized coating.

In accordance with another embodiment of the skin contact device of the present invention, the film layer is selected from the group consisting of polyether block amides, thermoplastic polyurethanes and polyesters.

In accordance with another embodiment of the skin contact device of the present invention, the medicament is contained in a reservoir defined by release means for controlled release of the medicament from the reservoir, the release means comprising an active agent permeable membrane layer formed on the inner surface of the medicament reservoir, whereby the reservoir is completely enclosed between the active agent permeable membrane layer and the occlusive layer, the reservoir including heat seal means heat sealing the active agent permeable membrane layer to the occlusive layer at a predetermined location thereon, with the vent means being located in the occlusive layer and the active agent permeable membrane layer solely at that predetermined location. In a preferred embodiment, the predetermined location comprises a geometrical pattern thereon.

In accordance with another embodiment of the skin contact device of the present invention, the medicament is disposed in a continuous layer. In a preferred embodiment, however, the medicament is disposed in a discontinuous layer comprising a medicament-coated portion and a medicament-free portion. Preferably, the medicament-coated portion comprises a geometrical pattern.

In accordance with a preferred embodiment of the skin contact device of the present invention, the vent means is located in the occlusive layer solely at locations corresponding to the medicament-free portion. In another embodiment, the geometrical pattern comprises a plurality of parallel strips of medicament.

BRIEF DESCRIPTION OF THE DRAWINGS

The present invention can be more fully understood and appreciated with reference to the following detailed description, which, in turn, refers to the Figures, in which.

DETAILED DESCRIPTION

Figure 1:
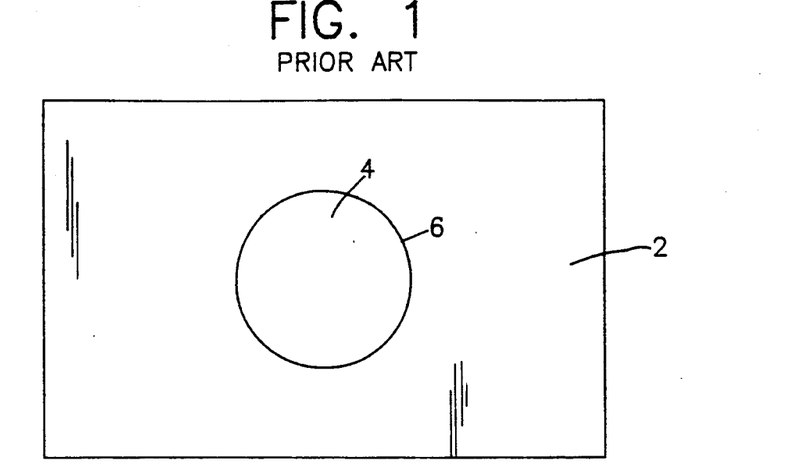
FIG. 1 is a top, perspective, elevational view of a skin contact device of the prior art.

Referring to the Figures, in which like reference numerals refer to like elements therein, and referring first to FIG. 1, a device, such as that shown in this Figure for the transdermal application of a medicament, includes a film layer 2 encompassing an occlusive layer 4 on its underside for placement against the skin. The underside of occlusive layer 4 would thus include an active agent or other medicament, as well as adhesive, enhancers, and the like. The underside of film layer 2 includes an adhesive layer for attaching the entire device to the patient's skin, with the occlusive layer below the film layer and against the skin for application of the drug or other medicament at required dosage levels.

The difficulty with devices such as that shown in FIG. 1, however, arises from the fact that the occlusive layer 4, although necessary to maintain the medicament or other active agent from escaping outwardly, i.e., in order to ensure that all of the drug is available for transdermal application, will also be occlusive for water vapor, which may thus build up within occlusive layer 4, i.e., between occlusive layer 4 and the skin. The degree of moisture build-up will be dependent upon a number of factors, including the period of time in which the device is intended to remain on the skin, the overall amount of active agent being applied, the degree of physical activity engaged in by the patients themselves, and the external circumstances of that activity, including the creation of additional moisture by the patient taking hot showers and the like, as well as the overall size of the occlusive layer, etc.

In any event, under normal circumstances, some amount of moisture which builds up within the occlusive layer 4 can migrate laterally, that is, towards the periphery 6 of the occlusive layer 4. Moisture passing outwardly from the periphery 6 can then create water vapor which, in turn, can pass through the film layer 2. However, again, based upon a number of the factors discussed above, in many circumstances the degree of removal of moisture by this method is insufficient to deal with the total amount of moisture created and retained within the area of the occlusive layer 4. When this occurs, the moisture itself can create bubbles and can begin to reduce the overall degree of physical contact between the skin and the active agent itself, and/or the adhesive which may be present at that location. Initially, reduction in such contact can have a deleterious effect in that reduced contact provides for reduced drug delivery to the skin. Even more significant, however, is the fact that further reduced contact not only exacerbates that problem, but also begins to reduce the overall contact with the entire device, and can, in fact, eventually result in the patch falling off completely.

On the other hand, the presence of a certain amount of moisture within the occlusive patch 4 is important for the operation of these devices. Thus, the moisture itself, in controlled amounts, is desirable in that it tends to mix with enhancer present in the active agents used therein to assist in the transdermal movement and application of same. The need thus exists for careful control of the moisture present within the device.

Figure 2:
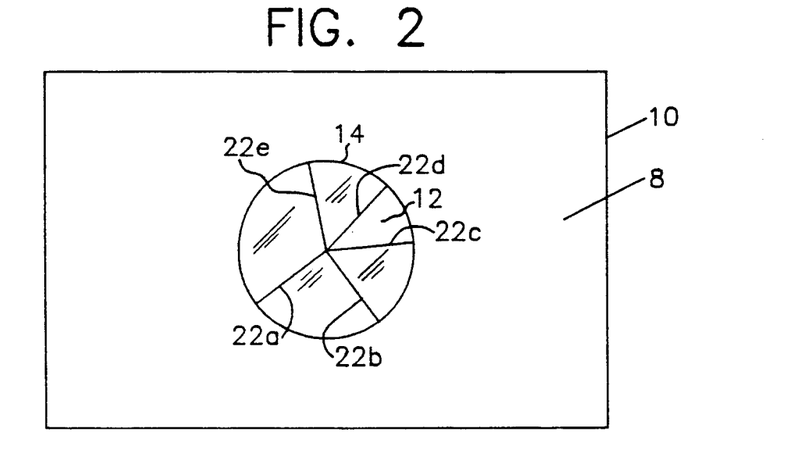
FIG. 2 is a top, perspective, elevational view of a skin contact device in accordance with the present invention.
Figure 3:
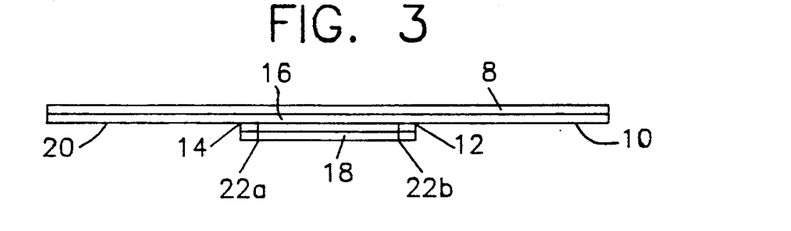
FIG. 3 is a side, elevational view of the skin contact device shown in FIG. 2.

Turning to FIG. 2, a device in accordance with the present invention is shown. The device again includes a film layer 8 having an outer periphery 10, and on whose underside is contained an occlusive layer 12 having an outer periphery 14. The occlusive layer 12 is affixed to the underside of the film layer 8 by means of an adhesive layer 16, as can best be seen in FIG. 3. On the underside of the occlusive layer 12 is preferably a layer of medicament 18 which is retained within the periphery 14 of the occlusive layer 12. However, reference numeral 18 can also correspond to an absorbent pad or the like; i.e., it need not necessarily comprise a medicament of any kind, although that is clearly a highly preferred embodiment of this invention. Without the medicament or other active agent, however, the moisture-removal properties of the present invention will still apply thereto.

In order to thus prevent water vapor and moisture build-up from occurring within the occlusive layer 12 to an extent greater than that which is desired, means for venting the water vapor are provided, and, in particular, as shown in FIG. 2, these include a number of narrow slits 22a–e which extend entirely through the occlusive layer 12. The pattern and number of these slits shown in FIG. 2 represents only one potential embodiment of the present invention, and is intended for illustrative purposes only. Thus, the precise number and location of the slits or apertures which extend through the occlusive layer 12 will ultimately depend upon the specific nature of the device in question and of the active agent or drug compound which is utilized therein. As can be seen from this device, however, the presence of these slits 22a–e permits water vapor at any given location within occlusive layer 12 to travel a far shorter path in its transverse movement under the occlusive layer 12 before it reaches a slit, i.e., as compared to the prior art where it was necessary to reach the outer periphery 6 in order to be located at a position where it was now possible to be released outwardly, in this case through the film layer 8. These slits or apertures comprising vents through the occlusive layer 12 can also take other forms, such as concentric rings, single apertures, or other such designs and shapes, as is discussed more particularly below in connection with the embodiments shown in FIGS. 6–8, and can also comprise a number of separate occlusive layer sections separated by interrupted areas where there is no occlusive layer thus constituting the vent means hereof, as discussed below in connection with the embodiment of FIG. 9.

Each of these embodiments of the invention is thus effective in controlling the moisture level within the occlusive layers thereof. By permitting the free passage of water vapor or moisture around and through the occlusive layer or portions thereof, the prior problems of moisture build-up and concomitant premature removal of the patch or other such device or film from the skin are effectively reduced if not eliminated. This, in turn, permits one to provide for longer term use, such as up to seven days or more, as compared to the one-day, or, at best, three-day patches which have prevailed in this industry.

In addition, the presence of the vent means of the present invention, such as the slits 22a–e shown in FIG. 2, provides an additional unexpected advantage. That is, the occlusive layer 12 is itself now articulated in that it can much more closely follow the contours of the area of skin at which it is located. This is particularly important when the device is placed in areas of substantial and/or constant movement, such as a hand or the like. The problem of the related stiff occlusive layer thus prematurely falling off in view thereof is thus significantly reduced hereby. This factor is particularly significant in connection with long-term use, again up to or greater than about one week, although it demonstrates these advantages even in connection with shorter term use patches.

It is also specifically noted that the presence of a number of these slits does not interfere with the basic function of this device, namely, to apply a medicament or other ingredient through the skin, or to act as a wound covering or wound dressing in the general sense. Thus, the presence of these slits will not permit significant loss of any drug which is present therewithin by escaping outwardly through the same slits as does the water vapor. The reason for this is that, as opposed to the water vapor, these medicaments and other active ingredients and drugs usable in connection with this invention do not generally migrate laterally, and thus there is only a minimal risk that a minor amount of the drug, which might be located precisely at a given slit, could possibly migrate outwardly and thus be released by passing through the film layer 8. This minor amount, however, can be taken into consideration in the initial construction of this device, i.e., by including a slightly greater amount within the occlusive layer 12 to compensate therefore, without any adverse consequences. Generally, the viscosity of the medicament layer, which, in many cases, includes enhancers, and an adhesive composition for attachment to the skin, and the like, is primarily responsible for the lack of migration of the drug materials contained therein.

In addition to the use of absorbent pads and/or various medicaments and active agents, the inner surface of adhesive layer 12 can also include various known absorbent hydrogels, either alone or in conjunction with an absorbent pad thereon. These hydrogels are generally prepared by copolymerizing and crosslinking both hydrophilic and hydrophobic monomers, such as hydroalkyl esters of acrylic and methacrylic acids, derivatives of acrylamide and methacrylamide, and N-vinyl-2-pyrrolidone, alkyl acrylates or methacrylates, vinyl acetate, acrylonitrile and styrene.

As is mentioned above, the presence of these slits or apertures has another entirely different advantageous consequence. That is, the occlusive layer 12 is generally considerably stiffer and less pliable than is the film layer 8, for example. This, in turn, can result in potential problems of loss of skin contact; i.e., the occlusive layer 12 cannot always follow the contour and/or movements of the skin at the particular site where it is located. However, the presence of slits 22a-e can result in the occlusive layer 12 having far greater flexibility and contour-following ability, or articulation, than was the case with a solid disc of occlusive material, thus resulting in even greater ability of this device to stay in contact with the skin.

The film layer 8 itself is a flimsy skin-tight material, which again allows air and moisture vapor to pass therethrough, but which will prevent the passage of bacteria or other undesired elements or materials.

It is preferred that film layer 8 thus be composed of various thin, plastic materials, or it can comprise an extremely thin foil layer, or layer of other non-woven materials, most particularly it will comprise a material which is sufficiently thin and flexible to be comformable to the skin, and will thus preferably be thinner than about 2 mils, preferably less than about 1.5 mils, and most preferably 1 mil or less.

These film layers 8 are preferably thermoplastic materials which are at least partially elastomeric in nature. They will therefore exhibit a high degree of elongation (preferably greater than about 130% elongation), and will thus exhibit excellent conformability characteristics without having the tendency to exhibit significant memory characteristics, although they will have some degree of recovery when stretched, for example. In terms of breathable films it is preferred that these materials, in addition to permitting air to pass therethrough, will also permit moisture vapor to pass through them, at least more readily than is the case with materials such as polyethylene, for example. All of these film layers must be occlusive, at least with respect to particulates, in order to protect the wound, etc. However, their overall occlusive characteristics can then vary, depending upon the ultimate use intended for them in each particular case. In general, however, it is preferred that films be employed which are permeable to various glycols, such as polyethylene glycols, but rather occlusive films can also be employed in selected circumstances including, for example, 1 and 2 mil layers of ethylene-vinyl acetate copolymers, or various nylon or polyester films. In addition, laminated or coated films could also be utilized, such as by employing a non-occlusive film such as those discussed above which is fully or partially selectively coated with an occlusive film.

The selection of the particular film which is to be employed in connection with this invention can also be made on the basis of the occlusive nature of the specific film selected therefrom. Thus, most particularly with respect to the occlusivity of the film with respect to moisture, these various films themselves will differ in that respect. In general, such films can now be produced which broadly range from about 100 to 20,000 or more $g/m^2$ in terms of the transmission of water vapor therethrough. Thus, selection of the appropriate thin film layer, while dependent on other factors, including strength, cost, occlusivity with respect to other ingredients, etc., can also be made with permeability to the water vapor itself in mind. One can thus balance the need to permit the moisture to escape for all of the reasons set forth above with a desire to nevertheless maintain a minimum moisture level therein. This is necessary in connection with certain drugs, for example, which require a certain degree of moisture in order to maintain a stable environment. It is also noted in this regard that, even with a particular thin film layer, such as the HYTREL material discussed below, polymeric blends can be formulated for this very purpose, i.e., of altering or controlling the moisture permeability thereof.

The various thermoplastic films themselves can generally be produced with either a matte, glossy, or a clear surface, which is obtained by selection or modification of the surface of the chilling roller generally used downstream of the film extruder from which the film is extruded, and they can include various colors, such as skin color, as well as fillers, such as $TiO_2$, clay, or other such materials for the purpose of rendering the film opaque, and various organic additives, odor inhibitors, and/or various medications, etc. directly on the surface thereof.

From the commercial viewpoint, one of the most successful high moisture vapor permeable medical grade elastomeric films has been one of a series of products marketed by Bertek, Inc., the assignee of the present application, under the designation "Medifilm 800." These films are extruded from a class of elastomeric resins which are polyether block amides, commercially designated by the trademark PEBAX. The structure of these polymers can be generally represented by the formula:

in which PA represents a relatively rigid polyamide segment and PE represents a relatively soft polyether segment. In this manner the extruded film products have high strengths in terms of high tear and abrasion resistance and at the same time provide a high degree of comfort or conformability, as well as moisture vapor permeability. The physical properties of two typical medical grade PEBAX films having a thickness of 1 mil are set forth in TABLE 1 herein.

TABLE 1

| PROPERTIES | FILMS | |
| --- | --- | --- |
| | MEDIFILM 810 | MEDIFILM 827 |
| Tensile strength - psi (ASTM D882) | 3120 | 2200 |
| % Elongation | 430 | 800 |
| Modulus @ 50% elongation | 1600 | 900 |
| Initial tear resistance - lbs. (ASTM D-1004) | 0.65 | 0.6 |
| MUTR - g/m²/24 hrs. (ASTM E-96) 37.8 C/90% R.H. | 1675 | 2200 |

In addition, other such film layers 8 can comprise thermoplastic polyurethanes which also meet the above requirements. These include such commercial polyurethane compositions as Dow Chemical Company's PELLETHANE, including its 2363-80AE grade thereof; K. J. Quinn's Q-THANE; B. F. Goodrich's ESTANE; Mobay Chemical Company's TXIN; and others. Furthermore, these film layers 8 can also comprise various polyesters, such as the copolymers of various cyclic polyesters including DuPont's HYTREL, including its 4056 grade thereof, and General Electric's LOMOD, both of which are copolymers of polyether prepolymers and polybutylene terephthalate and polyisobutyl terephthalate, respectively, as well as Eastman Chemical's PCCE.

In order to adequately maintain the film layer 8 on the surface of the skin of the patient, a layer of adhesive 20 is required on the underside of film layer 8, as can best be seen in FIG. 2. Since the film layer 8 is preferably being applied to the skin, the adhesive layer 20 should be hypoallergenic in nature. In addition, it is important in many circumstances that the adhesive used is entirely compatible with the drug or drugs which may be used in connection with this system, as well as being resistant to alcohol or other solvents which might be used therein. In a preferred embodiment of the adhesive layer 20, an acrylic copolymer adhesive such as Avery Chemical Company's AS-351 HSX can be utilized, preferably at a coating weight of between about 25 and 35 g/m². This pressure-sensitive adhesive is a crosslinkable polymer which dries to provide a permanently tacky film having a total solids content of about 52%, a Brookfield viscosity (LVT/04/12 RPM @ 25° C.) of from about 15,000 to 25,000 cps and a weight per gallon of about 7.4 lbs. It an also be diluted with hexane or toluene to a desired solids and/or viscosity range, particularly for use in conventional coating equipment.

As for the nature of the occlusive layer 12 itself, this layer is preferably a thin film or sheet and is occlusive with respect both to the active drug or agent or other medicament contained therewithin, as well as being impermeable to the adhesives used therewith, and to the moisture or water vapor discussed above. Thus, as indicated above, the principal purpose of this occlusive layer 12 is to prevent seepage of the active agent through the outer layer of the device. Within that context, a number of materials are suitable for these purposes, including, for example, cellophane, plasticized vinyl acetate-vinyl chloride copolymers, ethylene-vinyl acetate copolymer, polyethylene terephthalate, polyethylene, polypropylene, polyvinylidine chloride, and aluminum foil. Polyvinylidine chloride or SARAN are preferred components therefore. In general, these materials must be either totally occlusive to the passage of both water vapor and the drug compositions in question, or have only a very small degree of permeability. Thus, these materials shall permit 0 g/m² of moisture and/or medicament to pass therethrough, up to a maximum of up to about 50 g/m².

As for the medicament 18 itself, this can constitute a wide variety of different systemic or topical preparations, as well as such medicaments in the form of a hydrogel, an enclosed active agent carrier, and the like. Individual medicaments or mixtures thereof, if desired, can be employed. Any drug which passes through the skin can be employed for internal administration of the device of the invention.

Suitable systemic drugs for administration by the claimed device include those useful in treating emesis and nausea as is described in U.S. Pat. No. 4,031,894, e.g., preferably, scopolamine.

Other suitable drugs include the coronary vasodilators described in U.S. Pat. No. 3,742,951, such as compounds having nitrate moiety. Some suitable coronary vasodilators as well as other suitable systemic drugs are disclosed in U.S. Pat. Nos. 3,996,934 and 4,573,996, and the portions of both of these describing same are incorporated herein by reference thereto. In addition, hydrogels can be employed. These can include any of the conventional hydrogels, such as those disclosed in U.S. Pat. No. 4,438,258, the disclosure of which is incorporated herein by reference thereto.

Figure 4:
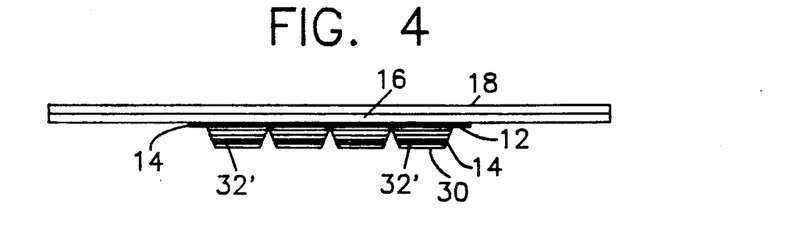
FIG. 4 is a side, elevational, sectional view of another skin contact device in accordance with the present invention.
Figure 5:
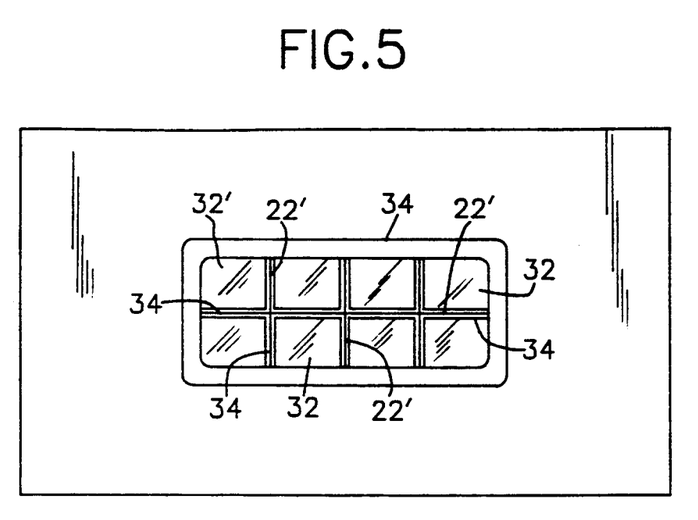
FIG. 5 is bottom, elevational view of the skin contact device shown in FIG. 4.

Turning to FIGS. 4 and 5, another embodiment of the present invention can be seen. In this embodiment, an active agent carrier is disposed on the underside of the film layer 8, with the active agent carrier being in the form known as a "ravioli" type. This includes an adhesive layer 16 on the inner surface of the film layer 8 and in contact with an occlusive layer 12 in contact therewith. The occlusive layer 12 is itself peripherally affixed to an active agent permeable membrane layer 30 about the entire periphery 14 of the occlusive layer 12. This is preferably accomplished by heat sealing the active agent permeable membrane layer to the occlusive layer about that periphery. Generally, between the active agent membrane layer 30 and the occlusive layer 12 is contained the medicament in a reservoir defined thereby. In this case, however, within this entire inner surface the medicament is divided into segregated medicament-containing portions 32', which can best be seen in FIG. 5. These medicament-containing portions 32' are defined by heat sealed areas 34 dividing the reservoir into these portions. Again, these heat sealed areas 34 seal together the active agent permeable membrane layer 30 and the occlusive layer 12 therealong. In this manner, the vent means comprising slits 22' can now be created within these heat sealed areas 34 without permitting direct release of any of the medicament therethrough. The membrane layer 30 itself is conventional in this art, and need not be discussed in detail here. Some preferred materials for a separate membrane layer may be, for example, polypropylene, polycarbonates, polyvinyl chloride, cellulose acetate, cellulose nitrate, and polyacrylonitrile.

Figure 6:
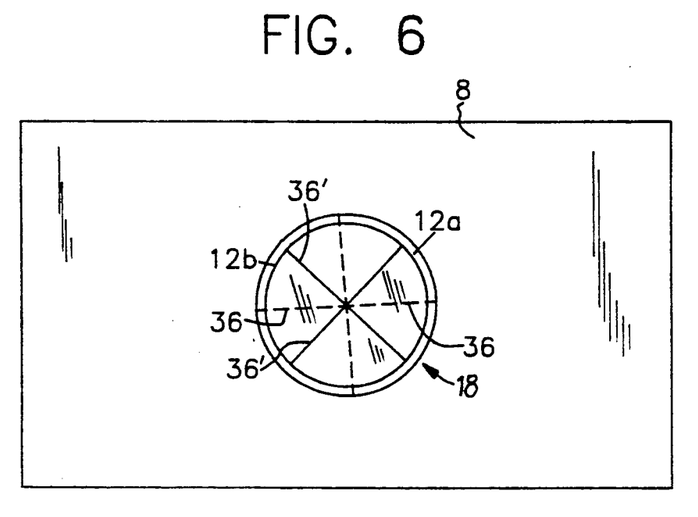
FIG. 6 is a top, perspective, elevational view of another skin contact device in accordance with the present invention.

Another embodiment of the present invention is shown in FIG. 6. In this embodiment, the inner surface of film layer 8 includes a first occlusive layer 12a which includes slits 36 shown in phantom view in FIG. 6, and occlusive layer 12a is then covered by a second occlusive layer 12b, including slits 36' therethrough, being attached thereto by conventional means such as an adhesive layer. Slits 36' are located in different locations than are the slits 36 in the first occlusive layer 12a; i.e., they are displaced from each other. Finally, the inner surface of the second occlusive layer 12b is covered by the medicament layer 18 for application to the skin.

Figure 7:
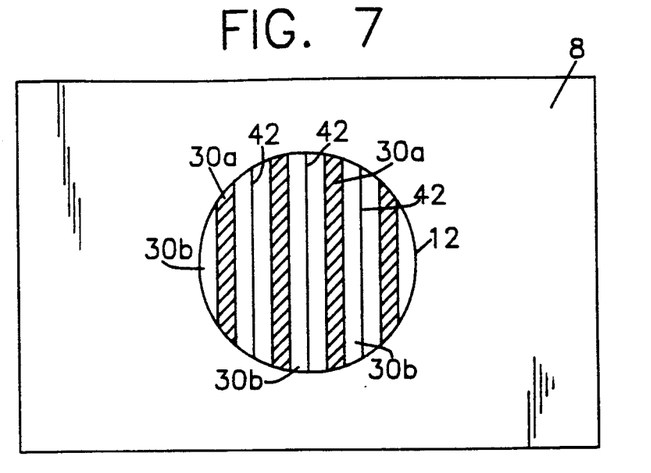
FIG. 7 is a top, perspective, elevational view of another skin contact device in accordance with the present invention.
Figure 8:
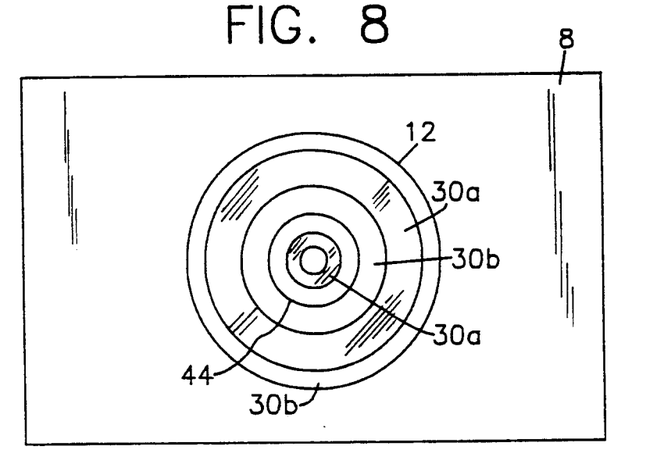
FIG. 8 is a top, perspective, elevational view of another skin contact device in accordance with the present invention.

Additional embodiments of the present invention are shown in FIGS. 7 and 8. In each of these embodiments, the layer of medicament on the occlusive layer is non-continuous, so that the occlusive layer 12 in each case includes medicament-containing areas 30a and medicament-free areas 30b. Thus, in the case of the embodiment shown in FIG. 7, the medicament-containing areas 30a comprise parallel strips crossing the entire area of the occlusive member 12, separated by the medicament-free areas 30b. In this case the vent means or slits 42 are contained within the medicament-free areas 30b. In the case of the device shown in FIG. 8, the medicament-containing areas comprise concentric annular rings 30a, and the medicament-free areas 30b comprise separate annular spaces therebetween. Again in this case the vent means or slit comprises a slit 44 within the medicament-free area 30b between the medicament-containing areas 30a. Thus, in these embodiments, the potential for even a small amount of medicament to escape outwardly through the slits and subsequently through the thin film 8 is substantially reduced to zero, because of the location of the medicament-containing areas and displacement from the location of the slits in question.

Figure 9:
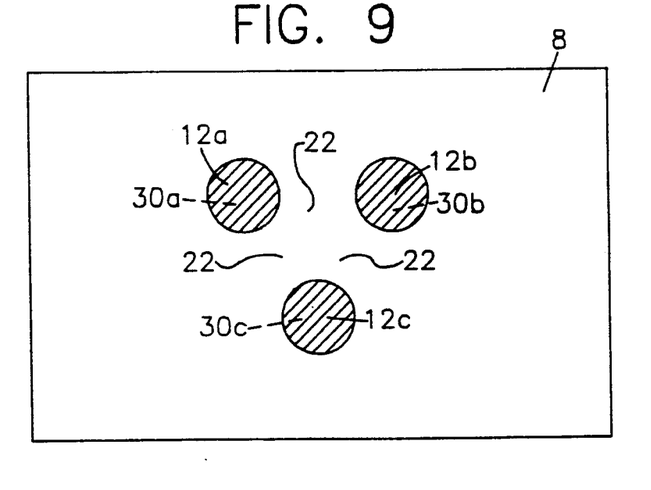
FIG. 9 is a top, perspective, elevational view of another skin contact device in accordance with the present invention.

Finally, an additional embodiment of the present invention is shown in FIG. 9. In this embodiment, the occlusive layer itself is not substantially continuous, but instead is divided up into a plurality of distinct occlusive layer portions or islands 12a–c. Each of these occlusive layer portions 12a–c can be applied to the film layer 8 in the same manner as the occlusive layer 12 is applied in accordance with the embodiments of this invention discussed above. Preferably, however, an entire or continuous such occlusive layer is first applied thereto, as in the case of the prior art device of FIG. 1, for example, and is then die-cut to provide the occlusive layer portions 12a–c, and simultaneously remove all of the occlusive layer portions therebetween, leaving the open spaces or areas 22 separating these is also non-continuous, in the sense that each occlusive portion 12a–c includes thereunder a separate medicament-containing area 30a–c, respectively. Indeed, this embodiment is particularly readily adaptable to the use of different medicaments in connection with the different occlusive portions thereof, without departing from the basic principles underlying this invention. In this embodiment the vent means hereof comprises the spaces 22 located between the occlusive layer portions 12a–c. Thus, with these small, individual islands of occlusive layers and medicament-containing areas, the moisture can migrate the relatively short distances towards these spaces 22, particularly as compared to the case with the single, large occlusive layer 4 of the prior art device of FIG. 1, and be free to then pass through the film layer 8 thereof.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A skin contact device for applying a medicament to the skin of a patient comprising a film layer which is thin and flexible and which is non-occlusive to the passage of water vapor, said film layer including an outer surface, an inner surface, and an outer periphery, an adhesive layer on said inner surface of said film layer for maintaining said film layer on said skin, at least one occlusive layer disposed on said inner surface of said film layer, said at least one occlusive layer including an outer surface in adhesive contact with said film layer and an inner surface carrying said medicament to be applied to said skin of said patient, said at least one occlusive layer being occlusive to the passage of water vapor and to said medicament and having an outer periphery contained fully within said outer periphery of said film layer, and vent means between said inner surface of said at least one occlusive layer and said film layer permitting the free passage of water vapor contained within said at least one occlusive layer through said vent means for passage through said film layer, while substantially preventing the passage of said medicament through said film layer.

2. The skin contact device of claim 1 wherein said at least one occlusive layer comprises a plurality of separate occlusive layer portions separated by said vent means.

3. the skin contact device of claim 1 including a medicament on said inner surface of said occlusive layer.

4. The skin contact device of claim 1 wherein said film layer is selected from the group consisting of polyether block amides, thermoplastic polyurethanes and polyesters.

5. The skin contact device of claim 1 wherein said medicament is disposed in a continuous layer.

6. The skin contact device of claim 1 including a membrane on the inner suface of said medicament for controlling the rate of said flow of said medicament to said skin.

7. The skin contact device of claim 1 wherein said at least one occlusive layer is substantially continuous except for said vent means.

8. The skin contact of claim 7 wherein said vent means comprises slit means extending through preselected portions of said at leats one oclusiave layer.

9. The skin contact device of claim 8 wherein said slit means comprises a plurality of slits extending through said at least one occlusive layer.

10. The skin contact device of claim 9 wherein said pluralityof slits includes a first plurality of slits extending radially from a central location at least one occlusive layer.

11. The skin contact device of claim 1 wherein said medicament comprises a systemic or topical drug composition.

12. The skin contact device of claim 11 wherein said systemic or topical drug composition includes a drug enhancer.

13. The skin contact device of claim 1 wherein said least one occlusive layer comprises a plurality of occlusive layers including a first occlusive layer and a second occlusive layer, said first occlusive layer including an outer surface in adhesive contact with said film layer and an inner suface, said second occlusive layer including an outer surface in contact with said inner suface of said first occlusive layer, and an inner suface including said medicament, said first and second occlusive layers being occlusive to the passage of water vapor to said medicament and having outer peripheries contained fully within said outer periphery of said film layer, and said vent means comprising first vent means between said inner suface of said first occlusiave layer and said film layer and second vent means between said inner surface of said second occlusive layer and said first occlusive layer permitting the free passage of water vapor contained within said second occlusive layer through said second vent means for passage through said first vent means through said film layer.

14. The skin contact device of claim 13 including a medicament on said inner surface of said second occlusive layer.

15. The skin contact device of claim 13 wherein said first vent means is maintained at a location which is displaced from the location of said second vent means, whereby said water vapor cannot pass directly from said first vent means to said second vent means.

16. The skin contact device of claim 13 wherein said first and second occlusive layers are substantially continuous except for said first and second vent means.

17. The skin contact device of claim 16 wherein said first and second vent means comprise slit means extending through preselected portions of said first and second occlusive layers.

18. The skin contact device of claim 17 wherein said slit means comprises a plurality of slits extending through said first and second occlusive layers.

19. The skin contact device of claim 1 including a release layer disposed on said inner surface of said at least one occlusive layer, said surface of said release layer in contact with said medicament comprising a releasable surface.

20. The skin contact device of claim 19 wherein said releasable surface comprises a siliconized coating.

21. The skin contact device of claim 1 including an active agent permeable membrane layer formed on the surface of said medicament, said medicament thereby being contained within a reservoir between said active agent permeable membrane layer and said at least one occlusive layer, said reservoir including heat seal means heat sealing said active agent permeable membrane layer to said at least one occlusive layer at a predetermined location thereon, said vent means being located in said at elast one occlusive membrane layer solely at said predetermined location.

22. The skin contact device of claim 21 wherein said predetermined location comprises a geometrical pattern thereon.

23. The skin contact device of claim 1 wherein said medicament is disposed in a discontinuous layer comprising a medicament-coated portion and a medicament-free portion.

24. The skin contact device of claim 23 wherein said vent means is located in said at least one occlusive layer solely at locations corresponding to said medicament-free portion.

25. The skin contact device of claim 23 wherein said medicament-coated portion comprises a geometrical pattern.

26. The skin contact device of claim 25 wherein said geometrical pattern comprises a plurality of strips of said medicament.

27. The skin contact device of claim 25 wherein aid geometrical pattern comprises a series of annular portions of said medicament.

* * * * *